United States Patent [19]
Saniez et al.

[11] Patent Number: 5,891,708
[45] Date of Patent: Apr. 6, 1999

[54] NUTRIENT COMPOSITION RESULTING FROM MAIZE STEEPING

[75] Inventors: Marie-Hélène Saniez, Saint-Andre; Pierre-Antoine Gouy, Perenchy, both of France

[73] Assignee: Roquette Freres, Lestrem, France

[21] Appl. No.: 593,204

[22] Filed: Jan. 29, 1996

[30] Foreign Application Priority Data

Jan. 31, 1995 [FR] France .................................. 95 01110

[51] Int. Cl.$^6$ ................. C12N 1/00; C12P 1/00; A23B 7/10; A61K 35/00
[52] U.S. Cl. ................. 435/243; 435/41; 426/52; 426/53; 426/54; 426/531; 424/115; 424/601
[58] Field of Search ..................... 424/115, 439, 424/442, 601; 426/531, 52, 53, 54; 435/243, 112, 41

[56] References Cited

U.S. PATENT DOCUMENTS

| | | | |
|---|---|---|---|
| 4,359,528 | 11/1982 | Devos et al. | 435/43 |
| 4,914,029 | 4/1990 | Caransa et al. | 435/101 |

FOREIGN PATENT DOCUMENTS

| | | |
|---|---|---|
| 0 321 004 | 6/1989 | European Pat. Off. . |
| 379 232 | 7/1990 | European Pat. Off. . |
| 0 577 294 | 1/1994 | European Pat. Off. . |
| 2140672 | 1/1973 | France . |
| 2.254.641 | 7/1975 | France . |
| 2464298 | 4/1981 | France . |
| 4-198080 | 7/1992 | Japan . |
| 1387998 | 3/1975 | United Kingdom . |
| WO 93/16175 | 8/1993 | WIPO . |

OTHER PUBLICATIONS

Chemical abstracts, vol. 117, No. 21, 23 Nov. 1992 Abstract No. 211601 & JP 04 198 080 (Mitsui Toatsu Chemicals, Inc.) July 17, 1992.
Analysis Biochemistry (1976) 72, 248.
Manuel d'Analyse Chimique Volumétrique, H. Mathieu, Zd. Masson, 1946, p. 398.
Cereal Chemistry, vol. 68, No. 3, 1991 Minneapolis US pp. 319–320.
Cereal Chemistry, vol. 68, No. 1, Jan.–Feb. 1991 Minneapolis US pp. 7–12.
Starke, vol. 26, No. 12, Dec. 1974 Weinheim DE, pp. 433–436.
Article by M.L. Anson published in 1939 in J. Gen. Physiol. 22, 79–89.

*Primary Examiner*—David M. Naff
*Assistant Examiner*—Deborah K. Ware
*Attorney, Agent, or Firm*—Larson & Taylor

[57] ABSTRACT

The invention relates to a new nutrient composition resulting from maize steeping. This composition comprises an inorganic phosphorous concentration to total phosphorus concentration ratio (Pi/Pt) of between 35 and 95%. The composition also comprises proteins in an amount which gives a value of less than or equal to 5 according to a C test. A process for producing a nutrient composition is also disclosed; wherein the process requires maize steepwater to be subjected to an enzymatic treatment with the aid of protease and phytase enzymes. Furthermore, the enzymatic treatment is performed on a steepwater whose dry matter content is between 5 and 50%, and pH between 3 and 5, at a temperature varying between 40° and 60° C. and for 4 to 16 hours.

10 Claims, 3 Drawing Sheets

NUTRIENT COMPOSITION RESULTING FROM MAIZE STEEPING

BACKGROUND OF THE INVENTION

The subject of the present invention is a nutrient composition resulting from maize steeping.

It also relates to the process for producing such a composition, as well as its application as culture medium in fermentation industries and as food or food additive in compositions intended for humans or animals.

Maize steeping constitutes the first stage in the extraction of starch in wet milling. It consists in maintaining the maize placed in silos for a given time in hot water containing a small quantity of sulphur dioxide in order to facilitate subsequent protein-cellulose-starch separation and to prevent, moreover, the growth of undesirable microorganisms.

During this operation, two essential phenomena occur simultaneously. On the one hand, the highly fermentable soluble matter contained in the maize grains are transferred into the steepwater. Moreover, the steeping conditions (presence of sulphites and reducing sugars, and the temperature level) are favourable to the rapid development of mainly lactic acid bacteria.

The main advantage of the steepwater, commonly called corn steep by persons skilled in the art is linked to their composition in relation to essential compounds which are derived from the transfer of this soluble matter. These compounds constitute factors which are favourable to the growth of the microorganisms and to the production of secondary metabolites, and they make steepwater an ideal source of nutrients in the fermentation industry.

Indeed, corn steep contains as easily assimilable carbon sources: sugars and organic acids, as nitrogen and carbon sources: amino acids and polypeptides and as sources of trace elements necessary for the growth of microorganisms: "buffering" agents and minerals.

In addition, it constitutes a relatively inexpensive substrate, compared with yeast extracts which represent the reference material in this field, and which are also used as animal and human food.

Moreover, it is known that the use of corn steep as replacement for complex nitrogen sources such as cotton or soya bean proteins makes it possible to substantially increase antibiotic production yields.

For use in fermentation, corn steep should be subjected beforehand to sterilization, of which the temperature and pH conditions as well as the duration are chosen so as to obtain the destruction of microorganisms.

Thus, the temperature is generally between 105° and 130° C. and the pH varies between 3.0 and 8.0. Now, these temperature and pH conditions cause the precipitation of certain constituents of corn steep, which causes numerous disadvantages.

Indeed, the use of such a nonhomogeneous corn steep poses a problem as regards its preparation, and in particular during its concentration. In addition, its use causes the formation of a large deposit on the walls of fermenters, which deposit risks blocking the temperature exchangers. Finally, the recovery of the fermentation products may be substantially disrupted following the blocking of the membranes and of the filters.

Among the solutions proposed to solve this problem, the oldest is that which consists in extracting from the corn steep, by chemical precipitation, the substances responsible for coagulation. Thus, the addition to corn steep of alkaline agents (calcium hydroxide, sodium hydroxide and the like) or of metallic compounds (especially aluminium salts), in order to cause the precipitation of certain proteins, sulphite or sulphate compounds or alternatively phytic acid, is known. However, in addition to the extra cost associated with this additional treatment, its major disadvantage is the removal of nutrients from the medium. Furthermore, such a treatment requires the introduction, into the corn steep, of chemical products in quantities which may be high, which considerably modifies its composition and thus limits its potential uses.

Ultrafiltration has also been used to separate from the maize steepwater the molecular species, especially proteins and peptides, which are heat-coagulable. This technique has in fact been the subject of a French patent No. 2,140,672 granted to the company SCHOLTEN-HONIG RESEARCH.

Finally, it has more recently been proposed to treat corn steep with enzymes.

Thus, U.S. Pat. No. 4,914,029 granted to the company DORR-OLIVER describes a treatment with a phytase-cellulase mixture.

However, while such a treatment makes it possible to avoid the precipitation of phytic acid, it is not sufficient to solve completely the problem of the formation of a precipitate during the sterilization of corn steep.

Moreover, a treatment with a protease is described in Japanese patent No. 04-198,080 filed by the company MITSUI TOATSU CHEMICALS: the action of such an enzyme on a corn steep contributes to the improvement of its filterability. Corn steep thus treated is intended for the preparation of a liquid fertilizer.

Likewise, M. ROUSHDI, Y. GHALI and A. HASSANEAN have studied the action of two proteolytic enzymes (Alcalase and Neutrase manufactured by the company NOVO) on maize steepwater in order to reduce the duration of the steeping operation and to obtain a starch having a reduced protein content.

However, it appeared that a treatment of corn steep with a proteolytic enzyme was not sufficient to satisfactorily eliminate the problems mentioned above.

Consequently, none of the treatments described and used up until now has made it possible to solve satisfactorily the problem posed by the formation of a precipitate during the sterilization of corn steep, that is to say without causing the loss of a substantial fraction of the constituents of corn steep.

SUMMARY OF THE INVENTION

Now, the applicant has just developed a corn steep whose nutritional qualities are intact, or even improved, and which withstands the chemical treatment made necessary by its use as fermentation medium, or as additive in animal or human food. In particular, the formation of a precipitate during the sterilization of corn steep is considerably reduced, to a level not obtained by any of the solutions proposed up until now.

In addition, this nutrient composition has the advantage of being capable of being concentrated above 60% dry matter without encountering a caking phenomenon, as in the case of the corn steeps of the prior art. Such a concentration makes it possible to confer on the nutrient composition according to the invention a very good stability and a viscosity which is perfectly adapted to the industrial conditions of use, such as especially the transfer by pumps. It also has an economic advantage, due to a reduction in the costs of storage and transportation, but also the costs generated by the evaporation stage. Indeed, the blocking of the corn steep evaporators at the level of the preheaters represents a major problem, to which the only solution currently provided consists in cleaning the evaporators and the piping using sodium hydroxide and nitric acid.

This economic advantage is also significant at the level of the drying stage for dry feeds for animals which are obtained from a composition according to the invention, for example by incorporating this composition into dry spent maize grains.

In addition to the economic advantage, there is in this case an ecological benefit since the olfactory nuisances associated with the drying are considerably reduced.

The invention therefore relates, firstly, to a nutrient composition characterized in that it has an inorganic phosphorus concentration to total phosphorus concentration ratio of between 35 and 95%, and in that the assay of the proteins which it contains, carried out according to a C test, gives a value of less than or equal to 5.

The inorganic phosphorus and total phosphorus concentrations are measured according to known methods such as those described below.

As regards the inorganic phosphorus, the reference method consists in measuring the absorbance, at a wavelength of 360 nm, of a complex obtained by the reaction between the inorganic phosphorus and ammonium molybdate, which absorbance is directly proportional to the quantity of inorganic phosphorus present in the sample. For the implementation of this method, it is possible to use for example the assay kit sold by the company GILFORD DIAGNOSTICS under the reference 722058.

As regards the total phosphorus, its assay is carried out according to the standard ISO 3946 method which is based on the same principle as that applied to the determination of the concentration of inorganic phosphorus, which is described above. A preliminary step is however carried out, which step consists in destroying the organic matter in the products to be assayed, by mineralization with the aid of a sulphonitric mixture and conversion of the phosphates to orthophosphates. The next steps consist in forming the molybdic complex and then in measuring the absorbance at a wavelength of 825 nm.

Preferably, the inorganic phosphorus concentration to total phosphorus concentration (Pi/Pt) ratio is between 60 and 95%, and still more preferably between 75 and 85%.

As regards the C test applied to the compositions according to the invention, it is intended to measure the concentration of protein per 100 grams of dry matter of the supernatant of these compositions.

For this, a spectrophotometric measurement of these supernatants placed in the presence of a coloured reagent is carried out according to the Bradford method, a method which is known for the assay of proteins and which is described especially in Analysis Biochemistry (1976) 72, 248.

In the present case, the reagent used is Coomassie Brilliant Blue G 250, manufactured by the company PIERCE under the reference 23200, and which has the characteristic of binding to proteins and to peptides of more than 20 amino acids in acidic solution, this binding being accompanied by a change of colour from red-brown to blue.

By measuring the absorbance at a wavelength of 595 nm, which absorbance corresponds to the amount of reagent bound to the proteins present and is consequently proportional to the quantity of proteins, and then comparing with a standard curve obtained for various concentrations of a standard protein (Bovine Serum Albumin, Ref. 23209 from PIERCE), the protein concentration of the supernatants of the compositions is determined.

To carry out this measurement, the nutrient composition to be tested is adjusted beforehand to a dry matter content of 30% by weight. It is then centrifuged at 5000 g for 15 min and the supernatant is recovered, and adjusted to a dry matter content of 25% by weight. The Bradford method is then applied to this supernatant by introducing the coloured reagent, mixing and then reading the absorbance.

The value obtained, which corresponds to the concentration of protein in grams per liter of supernatant, is then converted to a concentration in gram per 100 g of supernatant dry matter.

The nutrient compositions which are the subject of the present invention are such that the concentration of protein in grams per 100 g of supernatant dry matter is less than or equal to 5.

The invention relates, secondly, to a process for producing a nutrient composition resulting from maize steeping which has the characteristics mentioned above.

This process consists in treating the maize steepwater with at least one protease and at least one phytase.

Surprisingly and unexpectedly, the applicant company has demonstrated that a combined treatment with at least one protease and at least one phytase gave particularly advantageous results which, logically, could not have been expected by a person skilled in the art. Indeed, the results of such a treatment do not correspond to the simple addition of the effects obtained following the treatment with a protease and those obtained after treatment with a phytase.

The applicant company has thus been able to demonstrate that a real synergy resulted from the combined treatment of the maize steepwater with such enzymes.

The process according to the invention consists in introducing at least one protease and at least one phytase, simultaneously or successively, into the maize steepwater, in allowing them to act, with stirring, for a period which depends on the type of enzymes and the quantities used, in monitoring, by sampling, the variation, over time, of the Pi/Pt ratio and the protein concentration, in then inactivating these enzymes, and then in concentrating the resulting composition by evaporation.

The first stage of the process according to the invention therefore consists in an enzymatic treatment.

This treatment is performed following the maize steeping stage, on a steepwater having a dry matter content of between 5 and 50%, and preferably between 10 and 20%, a pH which is between 3.0, and 5.0, and a temperature varying between 40° and 60° C.

According to a preferred embodiment of the invention, the enzymatic treatment will be applied to steepwater obtained under the conditions described in French patent no. 79 22106, which already has a composition favourable to subsequent use in the fermentation industries.

The order in which the enzymes are introduced is not very important: thus, the protease treatment may proceed or follow the phytase treatment. Likewise, both types of enzymes can be used simultaneously.

The quantities of enzymes used depend on the activity specific to the enzyme chosen and on the conditions for its use (type of substrate, substrate concentration, pH, temperature, duration of treatment).

These quantities are between 0.1 and 2.0% relative to the dry matter content of the medium as regards the protease and between 0.01% and 0.1% as regards the phytase, which corresponds to a range of 0.06 AU to 1.2 AU per 100 g of dry matter of the medium and as regards the protease, and 50 to 500 PU per 100 g of dry matter of the medium as regards the phytase.

Anson unit (AU) is the protease unit, defined as the quantity of enzyme which, at its optimum pH and temperature, hydrolyses haemoglobin to produce 1 micromole tyrosine per minute according to the colorimetric method using the Folin Clocalteu reagent. (For a detailed description of this method, reference can be made to the article by M. L. ANSON published in 1939 in J. Gen. Physiol 22, 79–89).

Phytase unit (PU) is defined as corresponding to the quantity of enzyme which, at a pH of 5.5 and a temperature of 37° C., liberates one micromole of inorganic phosphorus per minute, from a solution of sodium phytate at 0.0015 mol/liter. (For a detailed description of this method, reference can be made to international patent application no. 93/16175).

The duration of the enzymatic treatment varies between 4 and 16 hours.

The treatment is preferably carried out with constant stirring.

The proteases which can be used in the process according to the invention are chosen in particular from acid proteases, such as those manufactured by the company BIOCON (ACID PROTEASE L B 59), by the company GIST BROCADES (PROTEASE A), by the company RÖHM (COROLASE PS), by the company GENENCOR (PROTEASE B99), or by the company NOVO (FLAVOURZYME).

The protease treatment may also result from the very presence, in the steepwater, of endogenous proteases, that is to say proteases generated by bacteria which have developed during the steeping operation.

As regards the phytases, there may be mentioned by way of example FINASE manufactured by the company ALKO, NATUPHOS 5000 marketed by the company BASF, or NOVO PHYTASE marketed by the company NOVO.

Commercial phytases and proteases are provided in the form of enzymatic preparations of fungal origin which possess, as a result, secondary enzymatic activities such as phosphatase, cellulase and lipase.

These "parasitic" enzymes, and in particular the phosphatases, participate advantageously in the treatment of the maize steepwater.

Samples of the reaction medium are taken at regular intervals in order to determine the inorganic phosphorus and total phosphorus concentrations, as well as the protein concentration using the C test.

When the Pi/Pt ratio reaches the minimum value of 35% and the protein concentration determined according to the C test becomes less than or equal to 5, the enzymatic reactions can be stopped by inactivating the enzymes.

For that, physical (temperature) and/or chemical (pH) means are used. Preferably, the reaction medium is subjected to heating at 80°–100° C. for a period of between 10 and 30 minutes.

In order to remove bacteria and in order to thereby obtain a clear product, the composition may be centrifuged or filtered over earth or over a microfiltration or an ultrafiltration membrane.

The process which is the subject of the present invention thus allows the production of a product whose dry matter content may be as high as 65%, which exhibits many advantages as described above.

The compositions according to the invention, by virtue of their nutritional characteristics, exhibit a specific advantage when they are used as fermentation substrate. They constitute, indeed, a substrate satisfactory for the production, under good conditions, of yeast, lactic acid bacteria, or of other microorganisms, but also of enzymes, antibiotics, amino acids, organic acids, vitamins or biopesticides.

They are also particularly suitable for the production of metabolites obtained using genetically modified microorganisms.

In addition, they are of interest to the food industry for their nutritional properties and for their flavour properties, and can thus be used as food or as taste enhancers in compositions intended for use as animal or human food.

DETAILED DESCRIPTION OF THE INVENTION

Figure 1:
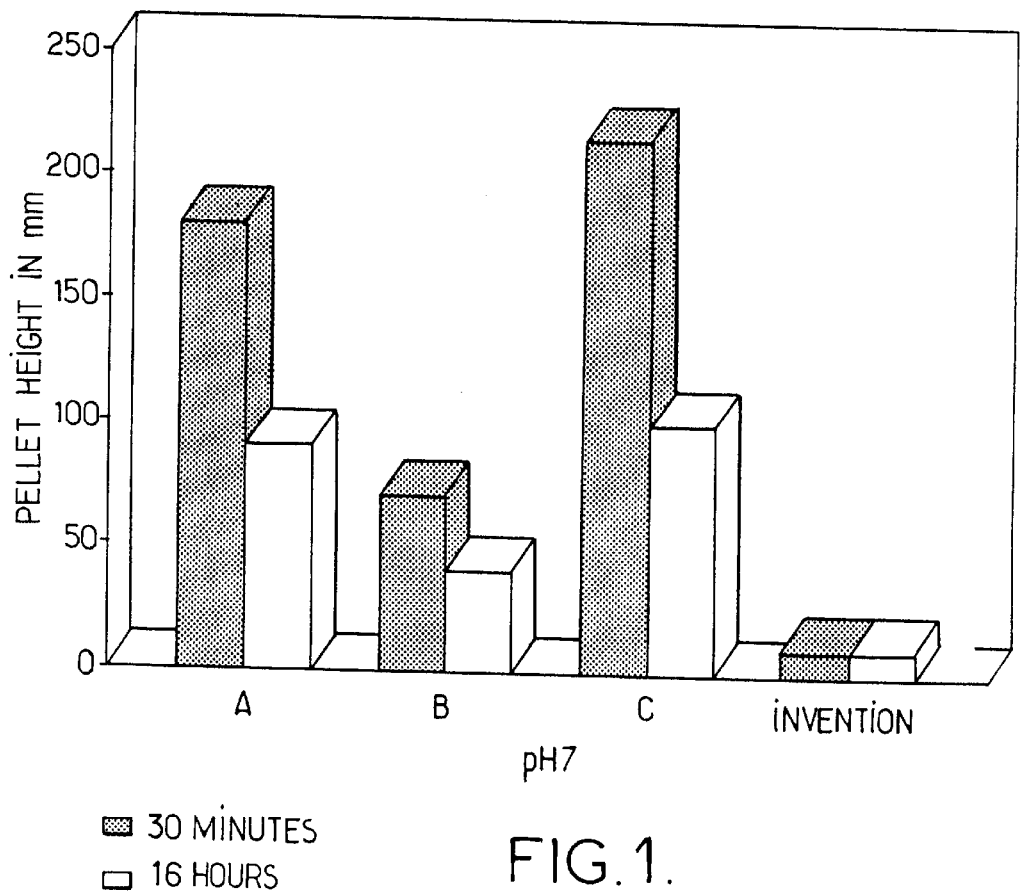
FIG. 1 shows the effect of enzymatic treatment on the height of the pellet obtained after decantation.

The examples given below illustrate the invention without however limiting it.

EXAMPLE 1

Manufacture of a nutrient composition according to the invention 1.5 liters of corn steep at 200 g/l of dry matter are introduced into a 2 liter reactor equipped with means for stirring and for regulating the temperature. The temperature of the substrate is adjusted to 50° C. and the stirring to 350 rpm. The pH of the product is not adjusted and therefore remains the natural pH of the corn steep, that is to say about 4.5.

To this substrate are added:
the phytase NATUPHOS 500 (BASF) at a level of 0.025% relative to the dry matter content of the substrate,
the protease ACID PROTEASE L B 59 manufactured by the company BIOCON, at the dose of 2% relative to the dry matter content of the substrate.

The duration of the reaction is 16 hours, during which the variation of the Pi/Pt ratio and the protein concentration are monitored by collecting samples from the reaction medium every 4 hours.

The enzymatic reactions are then inactivated by heating at 90° C. for 20 minutes and then cooling to room temperature. The resulting product is then centrifuged at 20° C. at a speed of 4500 g for 15 minutes. The pellet, which essentially consists of lactic acid bacteria, is removed and the supernatant is concentrated in a laboratory evaporator to a dry matter content of 60%. The product obtained is then cooled to room temperature, with stirring.

The composition obtained according to the process described above has a Pi/Pt ratio of 80%.

The protein assay carried out according to the C test gives a value of 2.2.

EXAMPLE 2

Manufacture of three compositions A, B and C according to the prior art

The composition A corresponds to a control corn steep at 200 g/l of dry matter which was not subjected to any enzymatic treatment.

The composition B is obtained according to the process described above, the only difference being that only the phytase NATUPHOS 5000 (BASF) was added to the substrate, at a level of 0.025% relative to the dry matter.

The composition C is obtained according to the process described above, the only difference being that only the PROTEASE ACID L B 59, manufactured by BIOCON, was added to the substrate at a level of 2% relative to the dry matter content of the substrate.

The Pi/Pt ratios and the protein concentrations measured according to the C test for each of the compositions A, B and C are given below:

|  | A | B | C |
|---|---|---|---|
| Pi/Pt | 20 | 80 | 20 |
| C test | 8.57 | 9.6 | 2.2 |

These three compositions are then concentrated to a dry matter content of 50%, which corresponds to the maximum value which can be obtained with these concentrations.

EXAMPLE 3

A—Demonstration of the physical stability of the nutrient compositions according to the invention The nutrient composition according to the invention as obtained in Example 1 is subjected to a settling test, compared with the three compositions A, B and C described in Example 2.

This test consists in measuring the height of the pellet after a previously sterilized composition has settled.

The composition according to Example 1 as well as the compositions A, B and C are first diluted to 25 g/liter, and then their pH is adjusted to a value of 7 by adding a 1N sodium hydroxide solution. This pH value corresponds to a maximum level of coagulation of the proteins.

These compositions are then subjected to sterilization by heating at a temperature of 120° C. for 20 minutes. They are then cooled, homogenized and then introduced into graduated measuring cylinders in which they are allowed to settle.

For each of the 4 compositions, the height of the pellet is measured after 30 minutes and after 16 hours.

The results obtained, which are shown in FIG. 1, are as follows:

| Composition | 30 min | 16 hours |
|---|---|---|
| Invention | 10 | 10 |
| A | 180 | 90 |
| B | 70 | 40 |
| C | 215 | 100 |

On reading these results, the superiority of the composition according to the invention appears clearly. Indeed, the pellet is considerably reduced compared with that observed after sterilization of the compositions according to the prior art, which were subjected to no enzymatic treatment, or to the treatments applied up until now, that is to say with a phytase not combined with a protease, or with a protease alone.

The advantage of the compositions according to the invention from the point of view of their stability to a sterilization treatment is clearly demonstrated here.

B—Comparative measurements of the viscosities of a composition according to the invention and of those of the three compositions according to the prior art The nutrient composition according to the invention, as obtained in Example 1, as well as the three compositions A, B and C described in Example 2, were subjected to a viscosity measurement with the aid of a BROOKFIELD viscometer and according to the procedure for using this apparatus.

The viscosity was measured at a dry matter content of 50%, therefore after prior dilution of the composition according to the invention.

Figure 4:
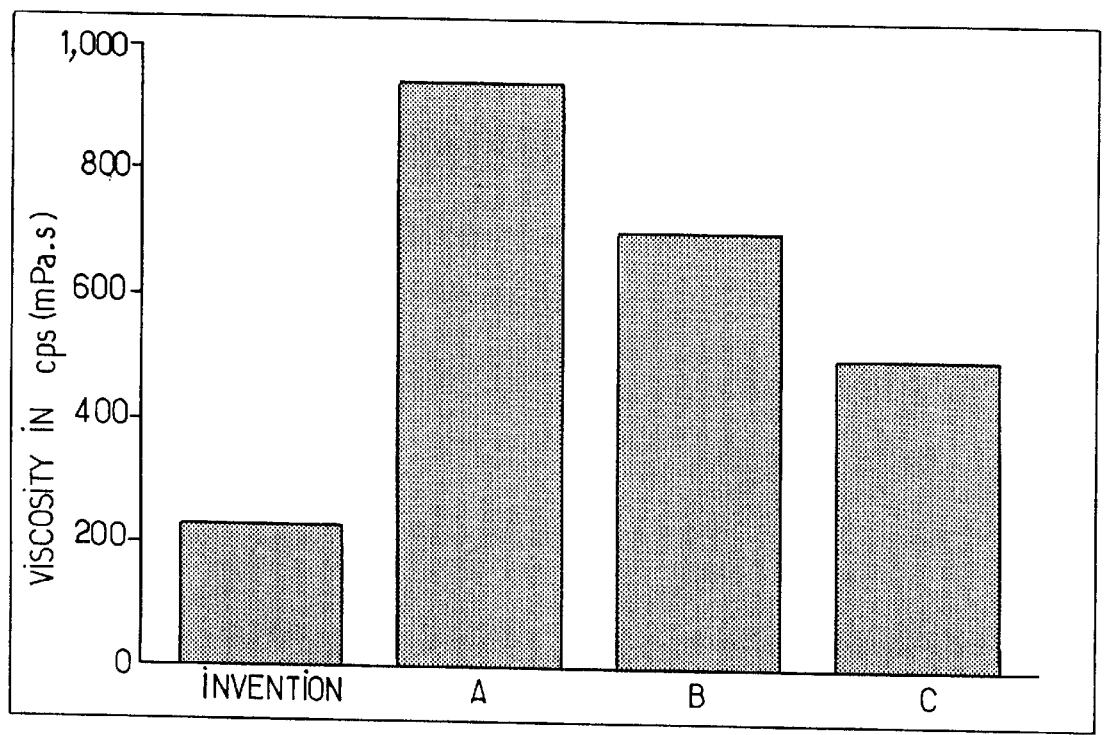
FIG. 4 shows comparative values of viscosity of different compositions.

The results, which are presented in FIG. 4, are given below.

| Composition | Viscosity in milliPascal.sec |
|---|---|
| Invention | 230 |
| A | 940 |
| B | 700 |
| C | 500 |

In addition, comparative measurements of viscosity were carried out at 55% and 60% dry matter between the composition according to the invention described in Example 1 and the composition A described in Example 2.

The results are as follows:

| Composition | Viscosity in milliPascal.sec at 55% DM | at 60% DM |
|---|---|---|
| Invention | 600 | 3,400 |
| A | 13,500 | solid appearance |

These results clearly demonstrate the superiority of the compositions according to the invention in their ability to be concentrated while remaining suitable for industrial use.

EXAMPLE 4

Demonstration of the good filterability of the nutrient compositions according to the invention The nutrient composition according to the invention, as obtained in Example 1, is subjected to a filtration test, in comparison with the compositions A, B, and C described in Example 2.

This test consists in measuring the time required for 10 ml of the test solution to pass through a filter consisting of an ashless paper disc 150 mm in diameter (PROLABO—Reference 08.313.766).

The dry matter content of the test solutions is adjusted to 25 g/l.

These solutions are subjected, after dilution, to sterilization by heat treatment at 120° C. for 20 minutes.

Their pH corresponds to the natural pH, that is to say 4.5.

Figure 2:
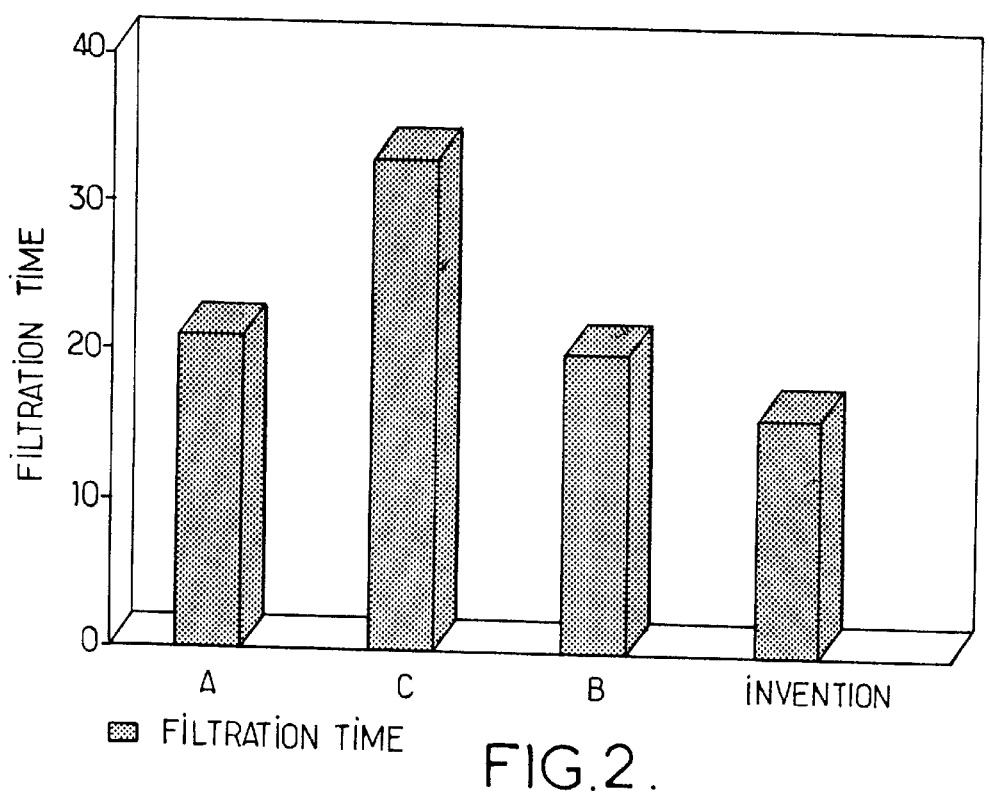
FIG. 2 shows the effect of the enzymatic treatment on filterability.

The values obtained, which are presented in FIG. 2, are as follows:

| Composition | Filtration time |
|---|---|
| Invention | 16 |
| A | 21 |
| B | 33 |
| C | 20 |

The filtration time for the composition according to the invention is considerably less than that obtained with each of the other three compositions, whether in the case of the control composition or of that subjected to an enzymatic treatment with phytase alone or with protease alone.

This clearly demonstrates the advantage of the compositions according to the invention and the efficiency of the phytase+protease enzyme treatment even after the heat treatment necessary for sterilizing the compositions.

EXAMPLE 5

Application of the compositions according to the invention to the growth of microorganisms The three studies described below consist in monitoring the increase in the number of cells as a function of time in culture media containing various concentrations of a nutrient composition according to the invention compared with a culture medium containing the same concentrations of the composition A, described in Example 2, which corresponds to a control corn steep which has not been subjected to any enzymatic treatment.

The first study relates to the yeast *Saccharomyces cerevisiae*.

Culture media are prepared by adding to demineralized water glucose in an amount of 10 g/l and nutrient composition as described in Example 1 and whose dry matter content has been adjusted to 50%, at respective concentrations of 3 g/l and 10 g/l (these concentrations correspond to respective nitrogen equivalents of 0.1 g/l and 0.33 g/l). Simultaneously and in the same manner, a culture medium is prepared containing respectively 3 and 10 g/l of the composition A described in Example 2.

100 ml of each of these media are then inoculated with 0.1% by volume of a preculture of the strain.

The incubation is carried out at 30° C., with stirring of 280 revolutions per minute, for 24 hours.

The enumerations are carried out at times 0, 8 hours and 24 hours on OGA (oxytetracycline-glucose-agar) medium marketed by BIOKAR DIAGNOSTICS.

The results obtained are assembled in the tables below.

Medium at 3 g/l of composition

| C.F.U./ml (colony forming unit) | 0 h | 8 h | 24 h |
| --- | --- | --- | --- |
| A | $5.1 \times 10^2$ | $3.5 \times 10^6$ | $2.8 \times 10^8$ |
| Invention | $3.6 \times 10^2$ | $9.1 \times 10^6$ | $2.1 \times 10^9$ |

Medium at 10 g/l of composition

| C.F.U./ml | 0 h | 8 h | 24 h |
| --- | --- | --- | --- |
| A | $2.8 \times 10^2$ | $5.8 \times 10^6$ | $5.2 \times 10^8$ |
| Invention | $3.5 \times 10^2$ | $1.4 \times 10^7$ | $1.9 \times 10^{10}$ |

The results obtained demonstrate the particularly advantageous nutrient qualities of the compositions according to the invention, compared with a corn steep-based medium not having the characteristics claimed.

Indeed, at a concentration of 3 g/l, the medium containing the claimed nutrient composition allows a multiplication of the cells which is 10 times higher, after 24 hours of incubation, than that containing a nutrient composition according to the prior art.

At a concentration of 10 g/l, the multiplication factor is about 2 after 8 hours, and about 50 after 24 hours of incubation.

The second study was carried out with the strain *Bacillus subtilis* under conditions identical to those which have just been described.

The culture media are prepared by adding glucose (10 g/l), salts (MgSO$_4$ and KH$_2$PO$_4$, both at 0.05 g/l) and nutrient compositions (composition according to the invention described in Example 1 and whose dry matter content has been adjusted to 50%, and comparative composition A described in Example 2), at 2.6 g/l, which corresponds to a nitrogen equivalent of 0.086 g/l.

The inoculation and incubation conditions are identical to those described above.

The enumerations are carried out at times 0, 8 and 24 hours on soyabean trypticase agar medium (DIFCO).

The results given below confirm the previous conclusions, namely the great advantage of the nutrient compositions according to the invention as fermentation substrate.

| C.F.U./ml | 0 h | 8 h | 24 h |
| --- | --- | --- | --- |
| A | $1.4 \times 10^2$ | $1.9 \times 10^6$ | $1.7 \times 10^8$ |
| Invention | $2.1 \times 10^2$ | $8.8 \times 10^6$ | $1.8 \times 10^9$ |

The third study was carried out with the strain *Lactobacillus plantarum* on three different culture media: the first containing a nutrient composition according to the invention, the second containing the composition A described in Example 2 and the third based on yeast extract, which constitutes the reference medium for the growth of microorganisms.

The first two culture media are prepared under conditions identical to those described above, by adding glucose (10 g/l) and a nutrient composition (composition according to the invention described in Example 1 and whose dry matter content was adjusted to 50%, and composition A described in Example 2), at 3 g/l, which corresponds to a nitrogen equivalent of 0.1 g/l.

The yeast extract-based medium is obtained by adding to demineralized water the yeast extract BACTO YEAST EXTRACT marketed by DIFCO, in quantities corresponding to a nitrogen equivalent of 0.1 g/l.

200 ml of each of the three media are then inoculated with 0.1% by volume of a preculture of the strain.

The incubation is carried out at 45° C. with gentle stirring (20 revolutions per minute) for 24 hours. The enumerations are carried out at times 0, 8 and 24 hours on MRS (MAN—ROGOSA—SHARP) medium marketed by BIOKAR DIAGNOSTICS.

The results obtained are assembled in the table below.

| C.F.U./ml | 0 h | 8 h | 24 h |
| --- | --- | --- | --- |
| Invention | $3.2 \times 10^2$ | $3.1 \times 10^6$ | $5.9 \times 10^8$ |
| Composition A | $3.7 \times 10^2$ | $8.3 \times 10^5$ | $8.1 \times 10^7$ |
| Yeast extract | $3.0 \times 10^2$ | $3.1 \times 10^5$ | $3.2 \times 10^7$ |

These results demonstrate once again the remarkable nutrient qualities of the compositions according to the invention compared with those of the prior art.

EXAMPLE 6

Application of the nutrient compositions according to the invention to the production of antibiotics The three studies carried out consisted in evaluating the production of three antibiotics, cephalosporin, penicillin and spiramycin, using as substrates a nutrient composition according to the invention, on the one hand, and a nutrient composition according to the prior art, on the other hand.

These productions are evaluated by the diffusion assay method (antibiogram) which consists in comparing the diameter for inhibition of the growth of a strain sensitive to this antibiotic, obtained with the sample whose antibiotic concentration is to be determined, with the diameter obtained with a range of known concentrations of the same antibiotic.

The first study, relating to the production of cephalosporin, can be outlined in the following manner:

The producing strain: *Cephalosporium acremonium,* after a preculture stage, is inoculated in an amount of 2.6% (volume/volume) into a production medium consisting of 50 g/l of glucose, 100 g/l of the nutrient composition according to the invention as described in Example 1 and whose dry matter content has been adjusted to 50%, as well as salts ($KH_2PO_4$ at 2.5 g/l and $CaCO_3$ at 5 g/l).

Simultaneously, the same procedure is carried out with a medium consisting of 50 g/l of glucose, 100 g/l of a nutrient composition of the prior art such as the composition A described in Example 2 and of the same salts at the same concentrations.

After incubating at 30° C. for 120 hours and with stirring of 120 revolutions per minute, centrifugation is carried out for the time necessary to obtain a clear supernatant which contains the cephalosporin produced.

Blotting discs are then impregnated with 65 μl of these supernatants and placed in a Petri dish on a soyabean trypticase agar medium and inoculated with the strain *Staphylococcus aureus* ATCC 6538, which is sensitive to cephalosporin.

The diameter of the growth inhibition zones obtained in both cases are then measured after incubating for 24 hours at 30° C.

The second study, relating to the production of penicillin, involves, as producing strain *Penicillium chrysogenum.*

This strain, after a preculture stage, is inoculated in an amount of 4% (volume/volume) into a production medium consisting of 120 g/l of lactose, 76 g/l of the nutrient composition according to the invention as described in Example 1 and whose dry matter content has been adjusted to 50%, as well as salts (($NH_4)_2SO_4$ at 10 g/l, $CaCO_3$ at 10 g/l, $KH_2PO_4$ at 0.5 g/l and $K_2SO_4$ at 5 g/l)).

Simultaneously, the procedure is carried out in the same manner with a production medium consisting of 120 g/l of lactose, 76 g/l of a nutrient composition of the prior art such as the composition A described in Example 2, as well as the same salts at the same concentrations.

After incubating at 25° C. for 6 days and with stirring of 220 revolutions per minute, centrifugation is carried out for the time necessary to obtain a clear supernatant which contains the penicillin produced.

As above, blotting discs are impregnated with 100 μl of these supernatants and deposited in Petri dishes containing a soyabean trypticase agar medium previously inoculated with the strain *Sarcina lutea* ATCC 9341 which is sensitive to penicillin.

The diameter of the growth inhibition zones obtained is then measured in both cases after incubating for 16 hours at 30° C.

The results obtained (expressed in millimeters) for each of these two studies are as follows:

|  | Cephalosporin | Penicillin |
| --- | --- | --- |
| Composition A | 21.00 | 20.00 |
| Invention | 29.00 | 26.00 |

Figure 3:
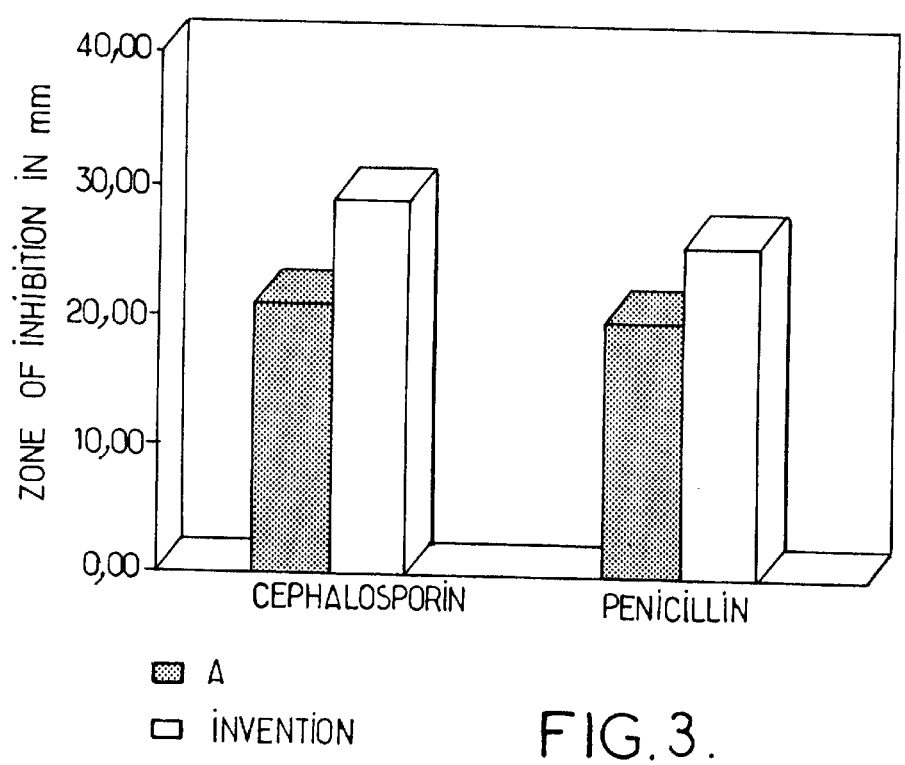
FIGS. 3 and 5 illustrate the production of antibiotics using the nutrient composition according to the invention.

These results are presented in FIG. 3.

The third study, which relates to the production of spiramycin, involves, as producing strain, *Streptomyces ambofaciens* (ATCC 15154).

This strain, after a preculture step, is inoculated in an amount of 5% (volume/volume) into a production medium containing 5 g/l of yeast extract, 20 g/l of soluble starch, 6 g/l of soyabean oil as well as salts (2.5 g/l of $KH_2PO_4$ and 5 g/l of $CaCO_3$).

80 g/l of the nutrient composition according to the invention and 80 g/l of the nutrient composition of the prior art such as the composition A described in Example 2, or alternatively a cotton protein solution such as that marketed by TRADERS PROTEIN under the name PHARMAMEDIA, corresponding to a nitrogen equivalent of 2.6 g/l, is added to this medium.

After incubating for 120 hours at 30° C. and with stirring of 120 revolutions per minute, centrifugation is carried out for the time necessary to obtain a clear supernatant, which contains the spiramycin produced.

As above, blotting discs are impregnated with 65 μl of these supernatants and deposited in Petri dishes containing a soyabean-casein-agar medium previously inoculated with the strain *Bacillus subtilis* DSM 347 which is sensitive to spiramycin.

The diameter of the growth inhibition zones obtained in both cases is then measured after incubating for 24 hours at 30° C.

The results obtained, which are expressed in mg/10 ml relative to a spiramycin calibration series establishing the correspondence between the diameter of the inhibition zone and the concentration of antibiotic produced, are as follows:

Composition 4.60

Invention 5.45

PHARMAMEDIA 4.00

Figure 5:
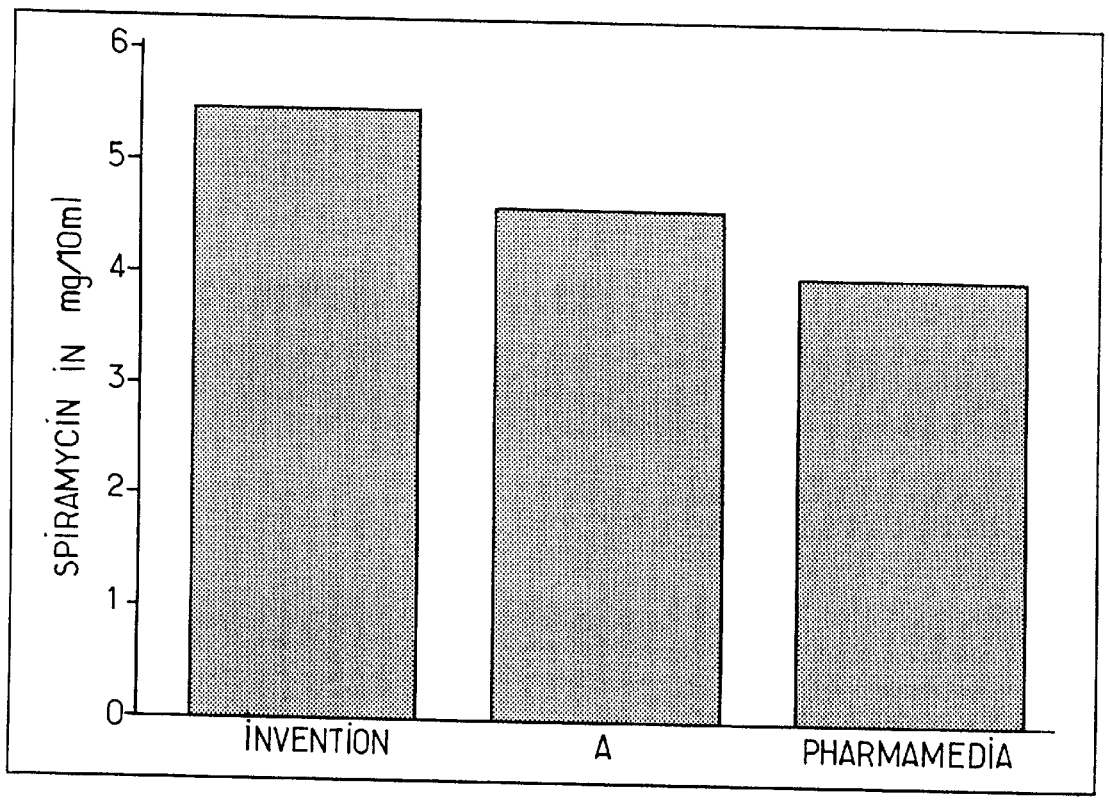

These results are presented in FIG. 5.

In the light of these results, the advantage of the nutrient compositions according to the invention in the production of metabolites and their superiority compared with those of the prior art are clearly demonstrated.

We claim:

1. Nutrient composition consisting essentially of fermented maize steepwater, having an inorganic phosphorus concentration to total phosphorus concentration ratio (Pi/Pt) of between 35 and 95%, and a protein concentration in a test C of less than or equal to 5.

2. Nutrient composition according to claim 1, having a Pi/Pt ratio between 60 and 95%.

3. Nutrient composition according to claim 1, having a dry matter content greater than or equal to 60%.

4. Process for producing a nutrient composition, said nutrient composition comprising an inorganic phosphorus concentration to total phosphorus concentration ratio (Pi/Pt) of between 35 and 95%, and a protein concentration in a test C of less than or equal to 5, said process comprising subjecting maize steepwater to an enzymatic treatment with at least one protease and at least one phytase, and subsequently recovering the enzymatically treated maize steepwater as the nutrient composition.

5. Process according to claim 4, wherein the enzymatic treatment consists of:
   a) introducing successively or simultaneously into the maize steepwater at least one protease and at least one phytase,
   b) allowing the protease and phytase to act, with stirring,
   c) monitoring, by sampling, variation over time of the Pi/Pt ratio and the protein concentration,
   d) inactivating the protease and phytase,
   e) concentrating the steepwater from step d) by evaporation, and
   f) recovering the steepwater from step e) as the nutrient composition.

6. Process according to claim 4, wherein the enzymatic treatment is performed on a steepwater whose dry matter content is between 5 and 50%, and pH between 3 and 5, at a temperature varying between 40° and 60° C. and for 4 to 16 hours.

7. Process according to claim 4, wherein the enzymatically treated maize steepwater is centrifuged and then concentrated to a dry matter content greater than or equal to 60%.

8. A medium for culturing microorganisms comprising the nutrient composition of claim 1.

9. A food or food additive for humans comprising the nutrient composition of claim 1.

10. A feed or feed additive for animals comprising the nutrient composition of claim 1.

* * * * *